United States Patent [19]

Wohrl

[11] 4,244,218
[45] Jan. 13, 1981

[54] FLUID MEASURING DEVICE

[75] Inventor: Josef Wohrl, Pfedelbach, Fed. Rep. of Germany

[73] Assignee: Eric Thomas Scriven, England; a part interest

[21] Appl. No.: 953,268

[22] Filed: Oct. 20, 1978

[51] Int. Cl.³ .......................................... G01F 23/10
[52] U.S. Cl. ..................................................... 73/309
[58] Field of Search .................. 73/309, 453, 194 E, 73/194 M; 177/207, 212

[56] References Cited

U.S. PATENT DOCUMENTS

| | | | |
|---|---|---|---|
| 988,342 | 4/1911 | Hillmer | 73/309 |
| 1,826,024 | 10/1931 | Roller | 73/309 X |
| 2,342,696 | 2/1944 | Rover | 73/309 |
| 2,966,172 | 12/1960 | Smith | 73/224 X |
| 2,993,625 | 7/1961 | Esval | 177/16 |
| 3,269,184 | 8/1966 | O'Connor | 73/309 |
| 3,527,096 | 9/1970 | Cohn et al. | 73/309 |
| 4,013,194 | 3/1977 | Moscarini | 73/233 |
| 4,039,036 | 8/1977 | Baumgartner et al. | 177/212 |
| 4,095,463 | 6/1978 | Wohrl | 73/141 |

FOREIGN PATENT DOCUMENTS 2235808  2/1974  Fed. Rep. of Germany ............ 73/141

*Primary Examiner*—Herbert Goldstein
*Attorney, Agent, or Firm*—Holman & Stern

[57] ABSTRACT

A fluid measuring device comprises a body suspended by a force transmission means within a container for receiving the fluid to be measured. The weight of the body is counterbalanced by a tare weight acting on a lever connected to the force transmission means. A gyroscopic load cell measures the vertical force exerted on the body by the fluid in the container and is calibrated so that a load cell display expresses the quantity of fluid received discharged or existing in the container as its volume or its weight. Servo-operable inlet and outlet valves to the container can be controlled by signals from the load cell whereby the device will meter predetermined quantities of the fluid.

14 Claims, 3 Drawing Figures

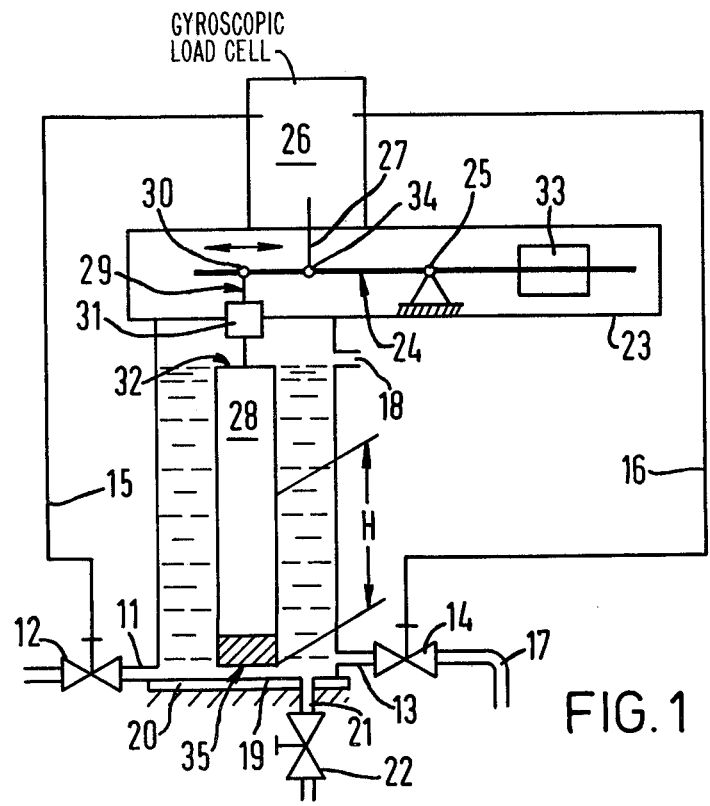
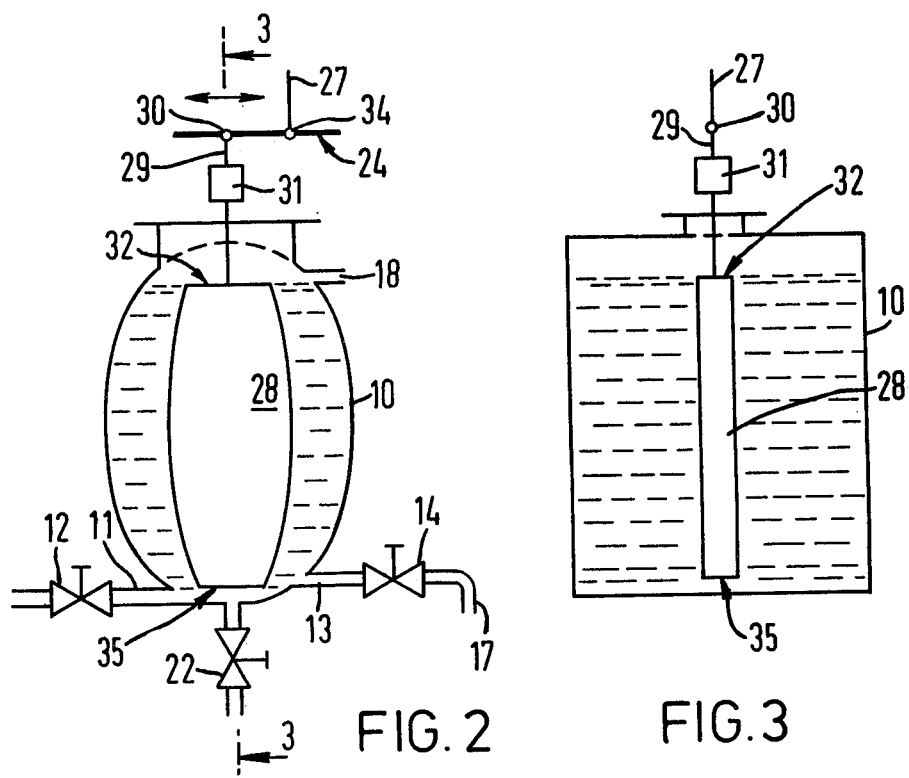
FIG. 1
FIG. 2
FIG. 3

FLUID MEASURING DEVICE

The present invention relates to an improved fluid measuring device. While the device is primarily intended for measuring the weight or volume of liquids received or delivered by the device it may also be applied to the measurement of density and surface tension forces and may be applied to other fluids such as heavy vapours and heavy gases.

BACKGROUND OF THE INVENTION

A device for measuring fluid consumption is known for example from German DAS 2319421 which discloses a balance using a two-armed balance beam of which one arm carries a measuring container and the other arm carries counter-weights for compensating the weight of the measuring vessel and the weight of the fluid at the start of the measuring process. In order to obtain respectable accuracy this device has to utilise light sources, photo-receivers and extensive electronic equipment. The primary disadvantage of this prior proposal is that its balance beam must support both the measuring container with its contents and also the counter-weights. The weighing beam therefore has to be of a correspondingly sturdy construction related to the weight of fluid to be measured. This proposal accordingly becomes increasingly unsuitable and ineffective as the weight of fluid to be measured increases.

The present invention is concerned with the provision of an improved device for fluid measurement which mitigates the above disadvantages whilst enabling very high accuracy to be achieved.

BRIEF SUMMARY OF THE INVENTION

The present invention relates to a fluid measuring device comprising a container for receiving the fluid to be measured; a body positioned within said container; a force transmission means retaining said body in a predetermined vertical position within said container irrespective of the fluid level in said container whereby said body is progressively immersed in the fluid when fluid is added to said container and said body progressively emerges from the fluid when fluid is withdrawn from said container, the cross-sectional area of said body at any fluid level within the operational range of the fluid measuring device having a known relationship with the cross-sectional area of said container at the same fluid level, and a load cell capable of measuring an applied force without movement of said force relative to said load cell, said force transmission means being connected to said load cell whereby the resultant vertical force on said body at any fluid level is transmitted to said load cell which is calibrated to take account of said known relationship and to express said resultant vertical force as a quantity of the fluid. When compared with the above-mentioned previously proposed device for measuring fluid consumption, the construction of the device provided by the present invention incurs considerably reduced structural complications and accordingly notably lower manufacturing costs. Furthermore the present invention also displays decisive advantages over the prior art insofar as it is particularly simple, is of extremely simple operation and has almost complete freedom from maintenance. Also, if this device is put in communication with a storage tank, it is possible to determine the degree of filling of the storage tank.

Another aspect of the invention is for the load cell to be additionally calibrated to take account of the density of the fluid and to express said resultant vertical force as a volume of fluid.

The cross-sectional area of said body at any fluid level within the operational range of the fluid measuring device may have a constant ratio to the cross-sectional area of said container at the same fluid level. In fact the cross-sectional areas of said body and said container are preferably constant throughout the operational range of the fluid measuring device.

A further aspect of the invention is for the load cell to be a gyroscopic load cell thereby enabling a continuous series of independent measurements to be made with exceptional accuracy and making possible the comparison of consecutive measurements to detect whether the measurement is steady or the integration of a series of measurements to provide a mean value.

Another aspect of the invention is for said force transmission means to be connected to said load cell through a linkage including a tare weight for compensating the weight of said body when the fluid level corresponds to a zero setting.

An outlet valve may be provided for controlling flow of fluid from the container, the load cell being calibrated to measure the quantity of fluid leaving the container. In this case the outlet valve may be servo-operable, the load cell being operatively connected to control the servo-operable outlet valve such that the servo-operable outlet valve will be closed when a predetermined quantity of the fluid has been delivered from the container.

An inlet valve may be provided for controlling flow of fluid into the container, the load cell being calibrated to measure the quantity of fluid entering the container. In this case the inlet valve may be servo-operable, the load cell being operatively connected to control the servo-operable inlet valve such that the servo-operable inlet valve will be closed when a predetermined quantity of the fluid has been received by the container.

BRIEF DESCRIPTION OF THE DRAWINGS

FIG. 1 is a vertical section taken through a fluid measuring device of the present invention, the view being generally diagrammatic.

FIG. 2 is a vertical section corresponding with the lower two-thirds of FIG. 1 but illustrating a modification of the container and body.

FIG. 3 is a section taken along the line 3—3 in FIG. 2.

DETAILED DESCRIPTION OF THE INVENTION

In the drawings like characters or reference numerals represent like or similar parts.

Referring to FIG. 1 a liquid container 10 is provided with an inlet 11 controlled by a servo-operable inlet valve 12 and with an outlet 13 controlled by a servo-operable outlet valve 14. The servo-operable valves 12 and 14 are magnetically-operable in response to an electronic operating signal via respective control lines 15 and 16. The servo-operable valves 12 and 14 may alternatively be of any known type. Inlet valve 12 controls the filling of the container 10 from an unshown storage tank through the inlet 11 and outlet valve 14 controls the emptying of the container 10 through the outlet 13 and a discharge conduit 17. The container 10 is also provided with an overflow 18 which controls the maximum liquid level within the container 10, any liquid passing through the overflow preferably being returned in any convenient manner to the storage tank. Conveniently the container 10 is of cylindrical form and is positioned so that its axis is vertical. The base 19 of the container 10 is consequently horizontal and is provided with a drainage channel 20 leading to a drainage passage 21 controlled by a stop-cock 22 which can be opened to enable liquid lying below the outlet 13 to be drained off. As shown by the cross-hatching, the base 19 is firmly supported by a rigid foundation or other rigid structure.

The top of the container 10 is open and communicates with the interior of a casing 23 which encloses a weighing linkage comprising a lever 24 pivoted from a supporting knife edge 25 carried by the casing 23. A gyroscopic load cell 26 of known construction is mounted on top of the casing 23. The construction may, for instance, be similar to that described in U.S. Pat. application No. 632,892, now U.S. Pat. No. 4,095,463 in which a gyroscope rotor is rotated by a motor at constant speed in an inner gyroscope gimbal that is pivoted in an outer gimbal supported for free rotation about its vertical axis. The force to be measured is applied by a vertical rod 27 through a swivel to a lever which reacts between the inner and outer gimbals to cause a primary precessional motion directly proportional to the applied force. Inaccuracies due to secondary precession are eliminated by means of a sensing device which identifies the associated movement of the vertical rod 27 and causes an auxiliary motor to apply a compensatory torque to balance the secondary precession. This gyroscopic load cell is capable of making exceptionally fine measurements of applied downwardly acting forces with no relative movement of the vertical rod 27 applying the force. The rate of primary precession is measured electronically and results in a series of consecutive independent measurements of the applied force. Each of these measurements can then be compared electronically with the preceding measurement such that the accepted value of the force will only be given when consecutive measurements are of the same value. The swivel connection between the vertical rod 27 and the lever reacting between the gyroscope gimbals is to ensure that the vertical rod 27 is not rotated by the primary precessional movement.

A cylindrical body 28 is positioned centrally within the container 10 with its axis vertical and is connected by a force transmission means, in the form of a vertical link 29, and a knife edge 30 to the lever 24. In this manner the body 28 is suspended within the container 10 by the vertical link 29 which serves to retain the body 28 in the vertical position illustrated irrespective of the liquid level in the container 10. The weight of the body 28 is chosen to be greater than the maximum weight of the liquid it displaces, that is when the liquid level coincides with the level of the overflow 18. To ensure that the body 28 remains vertical it is preferred to make a lower portion of considerably higher density that the remainder of the body 28. Instead of using the higher density lower portion, a tension spring could be connected, for instance by universal joints, between the bottom end of the body 28 and the container base 19 or a depression formed for the purpose in the container base 19.

The container 10 and the body 28 are carefully manufactured to ensure that their respective horizontal cross-sectional areas are constant throughout the operational range of the device, which range can extend between the levels of the outlet 13 and the overflow 18.

The maximum liquid level in the container 10 is preferably the level of the overflow 18 as illustrated although a lower level may be selected if so desired. A very fine length adjuster 31 is preferably incorporated in the vertical link 29 so that the level of the top end face 32 of the body 28 can be adjusted precisely relative to the maximum liquid level. Although the top end face 32 can be adjusted to be exactly level with the maximum liquid level, there is the possibility of inaccurate readings due to the possibility of the top end face 32 becoming wetted with the liquid and due to the loss of any vertically directed surface tension force when the top end face 32 is exactly level with the maximum liquid level. For this reason it is preferred to adjust the level of the top end face 32 to be slightly above the maximum liquid level.

The weight of the body 28 is counterbalanced by a tare weight 33. As the gyroscopic load cell 26 only measures downwardly acting forces, this is achieved when the liquid is at the maximum set level when it is arranged for the moments of the body 28 and of the tare weight 33 about the knife edge 25 to be in equilibrium. To facilitate fine adjustment of this equilibrium during installation, the tare weight may be mounted for fine adjustment axially along the lever 24. The moment of the surface tension acting on the body 28 can also be balanced at the same time. It will be noted that the vertical load applying rod 27 for the gyroscopic load cell 26 is connected to the lever 24 through a further knife edge 34. The equilibrium position at the maximum set fluid level can therefore be determined by adjusting the axial position of the tare weight 33 until the load cell 26 gives a zero reading.

If other types of load cell capable of measuring an applied force without relative movement of the force are used, the equilibrium position could alternatively be achieved when the body 28 lies wholly or mainly above the liquid level. In this connection it is considered best for the bottom end face 35 to be immersed in the liquid so that surface tension forces can again be counterbalanced. This alternative basis for equilibrium could also be used for a gyroscopic load cell if its load applying rod 27 were repositioned between the knife edge 25 and the tare weight 33, or some other means were used for reversing the direction of the applied force on the load applying rod 27.

In order to maximise the operational range, the bottom end face 35 is preferably at least level with the level of outlet 13 and the discharge conduit 17 is designed so that liquid can drain away to this level.

Variations in the liquid level in the container 10 cause corresponding variations in the volume of fluid displaced by the body 28, and the force applied by the vertical link 29, through the lever 24 and the vertical rod 27, to the gyroscopic load cell 26 is proportional to the weight of the liquid displaced by the body 28.

In the case where the zero datum is the maximum liquid level, the device is calibrated by filling the container 10 through the inlet valve 12 until the liquid reaches the maximum liquid level. The tare weight 33 is then adjusted as previously described to give a zero reading. Liquid is then removed through the outlet valve 14 down to the immersion depth H and the removed liquid is carefully collected and its exact weight is established using a second balance. Unless the load cell 26 is correctly calibrated, its display will now indicate an incorrect weight for the removed liquid. The knife edge 30 is now adjusted axially along the lever 24 to alter the leverage ratio until the display of the load cell 26 gives the correct weight. This adjustment of the knife edge 30 will slightly disturb the counterbalancing by the tare weight 33 and it will be necessary to refill the container to the maximum liquid level and readjust the tare weight to give a zero reading again. The process is then repeated until no further adjustment of the knife edge 30 is required. Liquid is then removed step-by-step at regular intervals and at each point the corresponding weight given by the display of the load cell 26 is checked by the second balance. The full operational range of the device can be confirmed in this manner. This calibration is useful when the device is for measuring the quantity of liquid delivered through the outlet valve 14. However, if the device is to measure the quantity of liquid delivered into the container through the inlet valve 12, the same procedure can be followed except that the maximum dischargeable quantity of liquid is set on the display of the load cell when the liquid is at the maximum level, the display being arranged to run backwards as the liquid is removed for comparison on the second balance. Conversely calibration may be effected from the minimum liquid level.

As the cross-sectional area of the body 28 remains constant throughout the operational range of the device, it will be noted that the vertical force exerted by the surface tension of the liquid on the body will remain constant at any given temperature thereby eliminating any surface tension error. The ability of the load cell to operate without relative movement of the applied force is of course most important as any movement of the applied force would cause a corresponding vertical movement of the body 28 and would falsify the result accordingly.

Although the device described so far is arranged to measure the weight of fluid received or discharged or existing in the container 10, this quantity may alternatively be expressed as a volume by appropriately providing for the load cell display to be calibrated to take account of the liquid's density. Conversely the load cell display would be calibrated to display the density of any fluid filling a predetermined volume of the container 10.

The electronics of the load cell display may also be provided with a floating zero facility so that the device will measure a quantity of liquid received or delivered from any starting point within the operational range of the device.

The electronics of the load cell may additionally be calibrated or programmed to give control signals for the control lines 15 and 16 to control the opening and closing of the valves 12 and/or 14 thereby causing the device to meter predetermined quantities of fluid by weight or by volume.

Although other forms of load cell could be utilised provided that they were capable of measuring an applied force without relative movement, particular advantages are gained by selecting a gyroscopic load cell. Apart from the exceptional accuracy of gyroscopic load cells, their ability to make a continuous series of independent force measurements and to compare consecutive measurements is useful. The independent nature of each measurement provides a fundamentally high certainty which is ideally suited for the dispensing of fluids. When liquids are moved rapidly, there is invariably surface disturbance such as ripples which tend to falsify the result. The series of independent measurements taken by a gyroscopic load cell can therefore be used either to detect when such disturbances have settled to a value which does not distort consecutive measurements or can, better still, be integrated electronically to give a much earlier estimate of the mean measurement.

Other forms of load cell which could be used include pressure cells requiring minimal strokes for their operation. Although such pressure cells could be used for some applications, their accuracy would seem to be inferior in several respects to gyroscopic load cells. Also weighing cells with an unchanging equilibrium position could conceivably be used.

Instead of being heavier than the maximum volume of fluid displaced, the body could be lighter.

Although the example of the invention described is designed for use with liquids, it is envisaged that it could be modified for use with other fluids and particularly heavy vapours and heavy gases. It is also envisaged that the device could readily be modified for measuring surface tension forces.

In the event that inflammable or explosive fluids are to be measured, the gyroscopic load cell 26 can be purged with air or an inert gas at a pressure slightly above atmospheric pressure to avoid any fire or explosion risk.

Referring to FIG. 2 and FIG. 3 it will be noted that the modification involves varying the cross-sectional area of the container 10 and the body 28 with the fluid level. The body 28 consists of a thin disk shaped so that its cross-sectional area at any level within the operational range of the device has a fixed proportion to the cross-sectional area of the container 10 at the same level, the exact relationship being determined by their respective profiles and the careful setting of their relative vertical positions by the operation of the very fine length adjuster 31. As the ratio is constant, the effects of the two shapes cancel each other out. However shapes of non-constant ratio could be used, if so desired, and the electronics of the quantity display unit driven by the load cell would then be calibrated accordingly.

The terminology used in this specification is for the purpose of description and not limitation, the scope of the invention being defined in the appended claims.

What is claimed is:

1. A fluid measuring device comprising:
   a container for receiving the fluid to be measured;
   a body positioned within said container;
   a force transmission means retaining said body in a predetermined vertical position within said container irrespective of the fluid level in said container whereby said body is progressively immersed in the fluid when fluid is added to said container and said body progressively emerges from the fluid when fluid is withdrawn from said container, the cross-sectional area of said body at any fluid level within the operational range of the fluid measuring device having a known relationship with the cross-sectional area of said container at the same fluid level, and
   a gyroscopic load cell capable of measuring an applied force without movement of said force relative to said load cell, said force transmission means being connected to said load cell whereby the resultant vertical force on said body at any fluid level is transmitted to said load cell which is calibrated to take account of said known relationship and to express said resultant vertical force as a quantity of the fluid.

2. A fluid measuring device as claimed in claim 1 wherein said load cell is additionally calibrated to take account of the density of the fluid and to express said resultant vertical force as a volume of the fluid.

3. A fluid measuring device as claimed in claim 1 wherein the cross-sectional area of said body at any fluid level within the operational range of the fluid measuring device has a constant ratio to the cross-sectional area of said container at the same fluid level.

4. A fluid measuring device as claimed in claim 1 wherein the cross-sectional areas of said body and said container are each constant throughout the operational range of the fluid measuring device.

5. A fluid measuring device as claimed in claim 1 wherein the weight of said body is greater than that of the maximum weight of the fluid that it displaces, and said body is suspended in said container by said force transmission means.

6. A fluid measuring device as claimed in claim 5 wherein said force transmission means is connected to said load cell through a linkage including a tare weight for compensating the weight of said body when the fluid level corresponds to a zero setting.

7. A fluid measuring device as claimed in claim 1 wherein an outlet valve is provided to control flow of fluid from said container and said load cell is calibrated to measure the quantity of fluid leaving said container.

8. A fluid measuring device as claimed in claim 7 wherein said outlet valve is servo-operable and said load cell is operatively connected to control said servo-operable outlet valve, said load cell being arranged to cause the servo-operable outlet valve to close when a predetermined quantity of the fluid has been delivered from said container.

9. A fluid measuring device as claimed in claim 1 wherein an inlet valve is provided to control flow of fluid into said container and said load cell is calibrated to measure the quantity of fluid entering said container.

10. A fluid measuring device as claimed in claim 9 wherein said inlet valve is servo-operable and said load cell is operatively connected to control said servo-operable inlet valve, said load cell being arranged to cause the servo-operable inlet valve to close when a predetermined quantity of fluid has been received by said container.

11. A liquid weighing device comprising:
a container for receiving the liquid to be weighed;
a body positioned within said container;
a force transmission means retaining said body in a predetermined vertical position within said container irrespective of the liquid level in said container whereby said body is progressively immersed in the liquid when liquid is added to said container and said body progressively emerges from the liquid when liquid is withdrawn from said container, the cross-sectional area of said body at any liquid level within the operational range of the liquid weighing device having a known relationship with the cross-sectional area of said container at the same liquid level,
a gyroscopic load cell which measures applied forces without relative movement of said forces, said force transmission means being connected to said gyroscopic load cell whereby the resultant vertical force on said body at any liquid level is transmitted to said gyroscopic load cell which is calibrated to take account of said known relationship and to express said resultant vertical force as a weight of the liquid, and
a servo-operable valve controlling the level of the liquid in said container, said gyroscopic load cell being operatively connected to control said servo-operable valve and being arranged to cause said servo-operable valve to close when the weight of liquid in said container has changed by a predetermined amount.

12. A liquid weighing device as in claim 11 wherein the horizontal cross-sectional areas of both the container and the body are constant throughout the operational range of the liquid weighing device whereby the liquid exerts a constant surface tension force throughout said operational range.

13. A liquid volume measuring device comprising:
a container for receiving the liquid of which the volume is to be measured;
a body positioned within said container;
a force transmission means retaining said body in a predetermined vertical position within said container irrespective of the liquid level in said container whereby said body is progressively immersed in the liquid when liquid is added to said container and said body progressively emerges from the liquid when liquid is withdrawn from said container, the cross-sectional area of said body at any liquid level within the operational range of the liquid volume measuring device having a known relationship with the cross-sectional area of said container at the same liquid level,
a gyroscopic load cell which measures applied forces without relative movement of said forces, said force transmission means being connected to said gyroscopic load cell whereby the resultant vertical force on said body at any liquid level is transmitted to said gyroscopic load cell which is calibrated to take account of said known relationship and the density of the fluid thereby to express said resultant vertical force as a volume of the liquid, and
a servo-operable valve controlling the level of the liquid in said container, said gyroscopic load cell being operatively connected to control said servo-operable valve and being arranged to cause said servo-operable valve to close when the volume of liquid in said container has changed by a predetermined amount.

14. A liquid volume measuring device as in claim 13 wherein the horizontal cross-sectional areas of both the container and the body are constant throughout the operational range of the liquid volume measuring device whereby the liquid exerts a constant surface tension force throughout said operational range.

* * * * *